US012629234B2

(12) United States Patent　　　(10) Patent No.:　US 12,629,234 B2

Emanuelli et al.　　　(45) **Date of Patent:　\*May 19, 2026**

(54) SYSTEM AND METHOD FOR MONITORING OPTIMAL DENTAL IMPLANTS COUPLEABLE WITH AN OPTIMIZED IMPLANT SITE

(71) Applicant: Silvio Franco Emanuelli, Sanremo (IT)

(72) Inventors: Silvio Franco Emanuelli, Sanremo (IT); Federico Manes, Sanremo (IT)

(73) Assignee: ISEMG S.R.L. (IT)

( \* ) Notice: Subject to any disclaimer, the term of this patent is extended or adjusted under 35 U.S.C. 154(b) by 96 days.

This patent is subject to a terminal disclaimer.

(21) Appl. No.: 18/814,170

(22) Filed: Aug. 23, 2024

(65) Prior Publication Data

US 2025/0032225 A1　　Jan. 30, 2025

Related U.S. Application Data

(63) Continuation of application No. 18/220,786, filed on Jul. 11, 2023, now Pat. No. 12,070,370, which is a (Continued)

(30) Foreign Application Priority Data

Feb. 17, 2017　(IT) ........................ 102017000017965
Feb. 17, 2017　(IT) ........................ 102017000017978
Jun. 21, 2017　(IT) ........................ 102017000069221

(51) Int. Cl.
　A61C 13/00　　　(2006.01)
　A61C 8/00　　　(2006.01)
　　　　(Continued)

(52) U.S. Cl.
　CPC .............. A61C 8/00 (2013.01); G16H 50/50 (2018.01); A61B 2034/101 (2016.02); A61B 2034/108 (2016.02); A61C 13/0004 (2013.01)

(58) Field of Classification Search
　CPC ........ A61B 2034/101; A61B 2034/104; A61B 2034/105; A61B 2034/108; A61C 13/0004; A61C 2007/004; A61C 8/00
　See application file for complete search history.

(56) References Cited

U.S. PATENT DOCUMENTS 8,562,338 B2　10/2013　Kitching et al.
9,111,372 B2　8/2015　Ortega et al.
　　　(Continued)

FOREIGN PATENT DOCUMENTS

DE　　102014215103 A1　2/2016
EP　　　1449489 A1　8/2004
　　　(Continued)

OTHER PUBLICATIONS

Avrampou, et al., "Virtual Implant Planning in the Edentulous Maxilla: Criteria for Decision Making of Prosthesis Design", Clinical Oral Implants Research, vol. 24, 2013, pp. 152-159.

(Continued)

*Primary Examiner* — Samuel S Hanna

(74) *Attorney, Agent, or Firm* — Condo Roccia Koptiw LLP

(57) ABSTRACT

A computer-implemented method for monitoring dental implant comprising the steps of graphically simulating an anatomy of a provided dental prosthesis coupleable to a dental implant; simulating an optimized implant site for the dental implant as a function of implant parameters of the dental implant and first parameters of the optimized implant site; calculating a plurality of optimal dental implants; selecting a usable implant from the plurality of optimal dental implants calculated; calculating first deviations between first parameters of the optimized implant site and first parameters of the usable implant; calculating second deviations between second parameters of the optimal dental implants not selected as usable implants and first parameters (Continued)

of the optimized implant site; calculating real optimized parameters of the optimized implant site as a combined function of first deviations and second deviations.

9 Claims, 11 Drawing Sheets

Related U.S. Application Data continuation of application No. 16/486,524, filed as application No. PCT/IB2018/050993 on Feb. 19, 2018, now Pat. No. 11,723,754.

(51) Int. Cl.
   *G16H 50/50*        (2018.01)
   *A61B 34/10*        (2016.01)

(56)                References Cited

U.S. PATENT DOCUMENTS

|  |  |  |  |  |
|---|---|---|---|---|
| 9,411,910 | B2 | 8/2016 | Methot | |
| 9,566,137 | B2 | 2/2017 | Hehn | |
| 11,045,293 | B2 | 6/2021 | Fisker et al. | |
| 2007/0099147 | A1 | 5/2007 | Sachdeva et al. | |
| 2009/0111071 | A1 | 4/2009 | Yau et al. | |
| 2009/0325127 | A1 | 12/2009 | Kusch et al. | |
| 2011/0136080 | A1 | 6/2011 | Holzner et al. | |
| 2012/0203366 | A1 | 8/2012 | Saliger et al. | |
| 2012/0239364 | A1* | 9/2012 | Glor | A61C 13/0004 |
|  |  |  |  | 703/11 |
| 2012/0282567 | A1 | 11/2012 | Nilsson | |
| 2014/0234803 | A1 | 8/2014 | Hehn | |
| 2014/0329194 | A1 | 11/2014 | Sachdeva et al. | |
| 2014/0342302 | A1 | 11/2014 | Kopelman et al. | |
| 2018/0206949 | A1 | 7/2018 | Jordan | |

FOREIGN PATENT DOCUMENTS

| | | | |
|---|---|---|---|
| EP | 2322114 | A1 | 5/2011 |
| JP | 2005168518 | A | 6/2005 |
| KR | 1020140005337 | A | 1/2014 |
| TW | 201108995 | A | 3/2011 |
| WO | 9926540 | A1 | 6/1999 |
| WO | 2007009719 | A1 | 1/2007 |
| WO | 2012004937 | A1 | 1/2012 |

OTHER PUBLICATIONS

Block, Micael S., "Dental Implants: The Last 100 Years", CrossMark, Journal of Oral and Maxillofacial Surgery, vol. 76, No. 1, 2018, pp. 11-26.

Buser, et al., "Optimizing Esthetics for Implant Restorations in the Anterior Maxilla: Anatomic and Surgical Considerations", The International Journal of Oral & Maxillofacial Implants, 2004, pp. 43-61.

Moon, et al., "Clinical Problems of Computer-Guided Implant Surgery", Maxillofacial Plastic and Reconstructive Surgery, vol. 38, No. 1, 2016, pp. 1-6.

Rajput, et al., "A Brief Chronological Review of Dental Implant History", International Dental Journal of Students Research, vol. 4, No. 3, Oct. 2016, pp. 105-107.

Rojas-Vizcaya, Fernando, "Biological Aspects as a Rule for Single Implant Placement. The 3A-2B Rule: A Clinical Report", Journal of Prosthodontics, vol. 22, No. 7, 2013, pp. 575-580.

* cited by examiner average(ΔBMij+)
average(ΔBMij−)
average(ΔBMij)

304A

PSIR

ΔUI

304B

PSIR

ΔUI

304C

PSIR

CROWN

PD

ID

A'

SI

A

GINGIVA

MAXILLARY
BONE
OM

Fig.4a

| II | |
|---|---|
| Tooth n° | 45 |
| Diameter | 3,7 mm |
| Lenght | 7,9 mm |
| Angle | 5° |
| Rating | 7 |

BMIi (i=0...2)

| BMI 0 | |
|---|---|
| Tooth n° | 45 |
| DIAMETER | 3,50 mm |
| LENGHT | 8,00 mm |
| ANGLE | 5° |
| BRAND | NOBEL BIOCARE |
| MODEL | Active |
| RATING | 7 |

| BMI 1 | |
|---|---|
| Tooth n° | 45 |
| DIAMETER | 3,75 |
| LENGHT | 7 mm |
| ANGLE | 5° |
| BRAND | NOBEL BIOCARE |
| MODEL | MKIII |
| RATING | 6 |

| BMI 2 | |
|---|---|
| Tooth n° | 45 |
| DIAMETER | 4,2 mm |
| LENGHT | 8,00 |
| ANGLE | 5° |
| BRAND | DENTSPLY |
| MODEL | Ankylos |
| RATING | 5 |

Fig.5

| SI | |
|---|---|
| Tooth n° | 45 |
| Diameter | 3,7 mm |
| Lenght | 7,9 mm |
| Angle | 5° |
| Rating | 7 |

| | UI | |
|---|---|---|
| UTn | Tooth n° | 45 |
| UDTn | DIAMETER | 3,50 mm |
| ULli | LENGHT | 8,00 mm |
| ULli | ANGLE | 5° |
| Ua | BRAND | NOBEL BIOCARE |
| Ub | MODEL | Active |
| Um | RATING | 7 |
| UR | | |

Fig.6

| SI | |
|---|---|
| Tooth n° | 45 |
| Diameter | 3,7 mm |
| Lenght | 7,9 mm |
| Angle | 5° |
| Rating | 7 |

| UI | | ΔUI II – UI |
|---|---|---|
| Tooth n° | 45 | 45 |
| DIAMETER | 3,50 mm | – 0,2 mm |
| LENGHT | 8,00 mm | + 0,1 mm |
| ANGLE | 5° | |
| BRAND | NOBEL BIOCARE | |
| MODEL | Active | |
| RATING | 7 | 0 |

| BMI 1 | | ΔBMIj II – BMI1 |
|---|---|---|
| Tooth n° | 45 | 45 |
| DIAMETER | 3,75 | + 0,05 mm |
| LENGHT | 7 mm | – 0,9 mm |
| ANGLE | 5° | |
| BRAND | NOBEL BIOCARE | |
| MODEL | MKIII | |
| RATING | 6 | 1 |

| BMI 2 | | ΔBMIj II – BMI2 |
|---|---|---|
| Tooth n° | 45 | 45 |
| DIAMETER | 4,2 mm | + 0,5 mm |
| LENGHT | 8,00 | + 0,1 mm |
| ANGLE | 5° | |
| BRAND | DENTSPLY | |
| MODEL | Ankylos | |
| RATING | 5 | 2 |

CI

PI

CROWN CO

DENTAL PROTHESIS PD

ALVEOLAR CREST

Pt1

CERVICAL MARGIN OF THE ALVEOLAR CREST

SO

CORTICAL

CORTICAL

α

APICAL MARGIN OF THE ALVEOLAR CREST

GINGIVA THICKNESS

MAXILLARY BONE OM

LOWER ALVEOLAR NERVE NAI

CROWN CO

CI

PROTHESIS PD

UPPER BONE MARGIN

CT ( CERVICAL MEASURE )

GINGIVA

Q1

MT

HR=Q1–Q2 su CL_3

Q3

ET ( APICAL MEASURE OF THE MANDIBULAR BONE )

Q2

HR

A–A'

LOWER ALVEOLAR NERVE NAI

MAXILLARY BONE OM

SYSTEM AND METHOD FOR MONITORING OPTIMAL DENTAL IMPLANTS COUPLEABLE WITH AN OPTIMIZED IMPLANT SITE

CROSS REFERENCE TO RELATED APPLICATIONS

This application is a continuation of U.S. patent application Ser. No. 18/220,786, filed Jul. 11, 2023, which is a continuation of U.S. patent application Ser. No. 16/486,524, filed Aug. 16, 2019, which is a National Stage Entry under 35 U.S.C. § 371 of Patent Cooperation Treaty Application No. PCT/IB2018/050993, filed Feb. 19, 2018, which claims priority from Italian Patent Application No. 102017000069221, filed Jun. 21, 2017, Italian Patent Application No. 102017000017978, filed Feb. 17, 2017, and Italian Patent Application No. 102017000017965, filed Feb. 17, 2017, the contents of which are hereby incorporated by reference herein.

This application is related to U.S. patent application Ser. No. 16/486,484 filed Aug. 15, 2019, and entitled "SIMULATION METHOD AND SYSTEM FOR AN OPTIMIZED IMPLANT SITE," and U.S. patent application Ser. No. 16/486,513 filed Aug. 16, 2019, and entitled "A METHOD AND SYSTEM OF IDENTIFYING A DENTAL IMPLANT FOR AN OPTIMIZED IMPLANT SITE," which are hereby incorporated by reference herein.

TECHNICAL FIELD

The present invention relates to a computer-implemented method for monitoring dental implants.

The present invention further relates to a system for monitoring dental implants.

In particular, the present invention relates to a method/system for monitoring dental implants coupleable to an optimized implant site.

BACKGROUND

At present, dental implants are designed and prepared according to the dentist's directions mainly on the basis of the experience gained.

Some guidelines suggest fairly coarse criteria to define the characteristic parameters of dental implants to be applied to patients.

It is an object of the present invention to provide a method/system for monitoring dental implants capable of defining plant parameters that guarantee stability and efficiency.

Another object of the present invention is to provide an easy-to-use monitoring method/system for dental implants.

A further object of the present invention is to provide a stable and efficient dental implant.

SUMMARY

The invention confers the main technical effect of identifying a real optimal dental implant in terms of structure, for example tooth identification code, sizing, for example diameter and length, and position, e.g. angle.

In particular, the invention, as described, achieves the following technical effects:

objective identification of a real optimal dental implant.

easy identification of a real optimal dental implant.

compliance of dental implant guidelines with optimal real values.

ability to couple 3D simulations obtained at different times, for example at the time of the first simulation and at the time of calculating real calculated parameters, by overlapping them for the purpose of evaluating parameters variation over time.

The mentioned technical effects/advantages and further technical/advantageous effects of the invention will be more clearly described in the following description of an embodiment provided by way of non-limiting example with reference to the attached drawings.

BRIEF DESCRIPTION OF THE DRAWINGS

FIG. 3A is a schematic view of a dental implant, according to the present invention.

FIG. 3B shows a reference system used in FIG. 3A.

FIGS. 4a, 4b, 5, and 6 show functions of the system/method, according to the present invention.

DETAILED DESCRIPTION

In the present description the following terminology will be used several times and kept as a reference also in the attached claims:

dental implant=screw entering the mandibular/maxillary bone;

implant site=cavity in the mandible/maxilla which receives the dental implant;

stump=pin that mates with the free end of the dental implant;

crown=tooth-shaped cover that mates with the free end of the stump;

dental prosthesis=set of stump and crown;

edentulous site=volumetric space intended to receive the dental prosthesis, in particular the space between two existing teeth;

vestibule=space between the cheeks and the gums;

mandible=bone that forms the lower scaffolding of the mouth; it houses the lower teeth in the maxillary arch and is the only moving part of the face;

jaw=bone that forms the upper scaffolding of the mouth and houses the upper dental arch.

Unlike the mandible, the jaw is a fixed bone, such that it doesn't move with the opening and closing of the mouth. Overall, the two bones are also referred to as maxillary bones and in the present description, the term maxillary bone OM will be used in this sense, i.e. without excluding that the example referred to a dental prosthesis applied to the inferior arch, excludes application to the upper arch.

The invention describes a method of monitoring dental implants and a corresponding system of monitoring dental implants.

Figure 1:
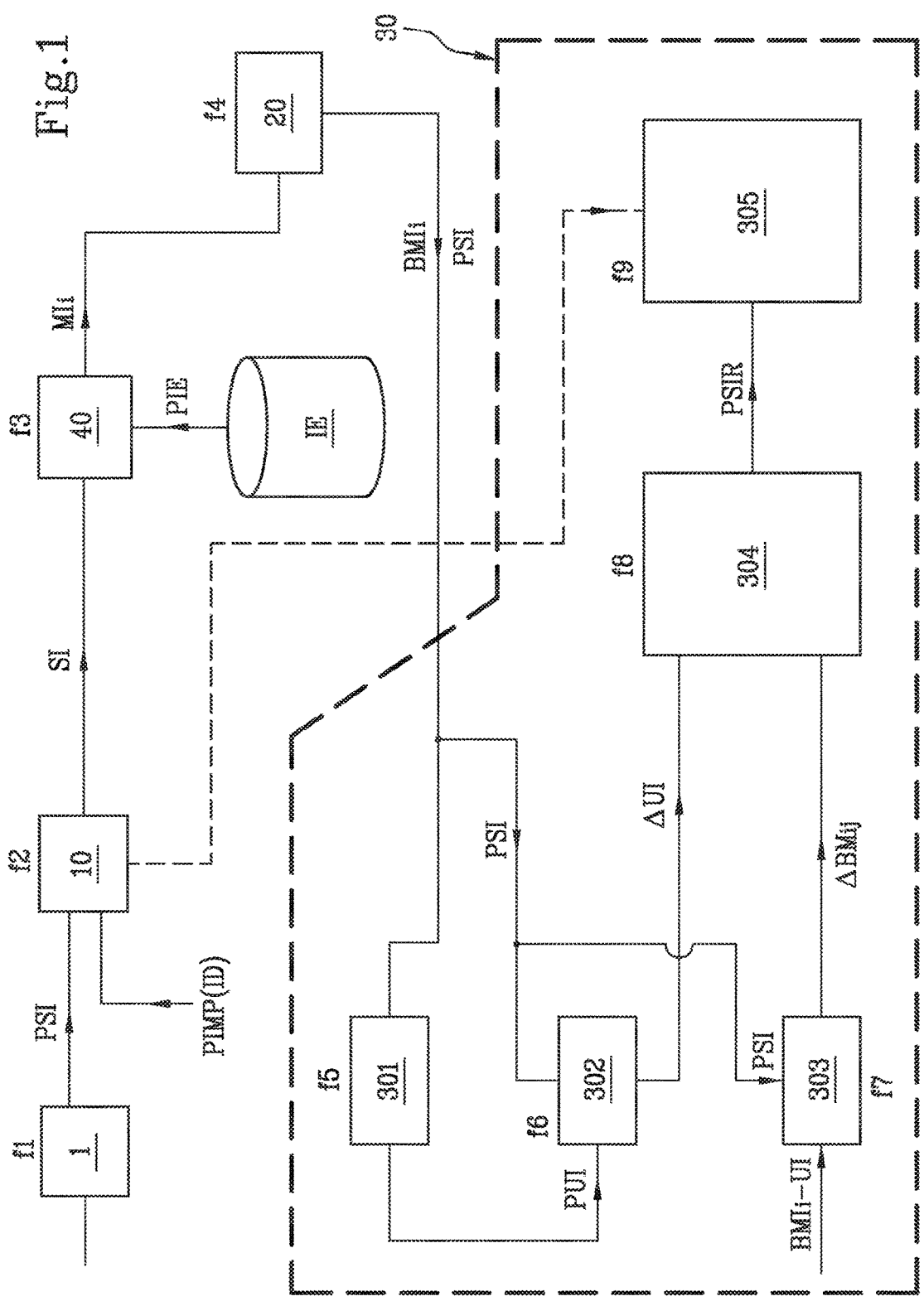
FIG. 1 is a block diagram of the system/method according to the present invention.
Figures 3A, 3B:
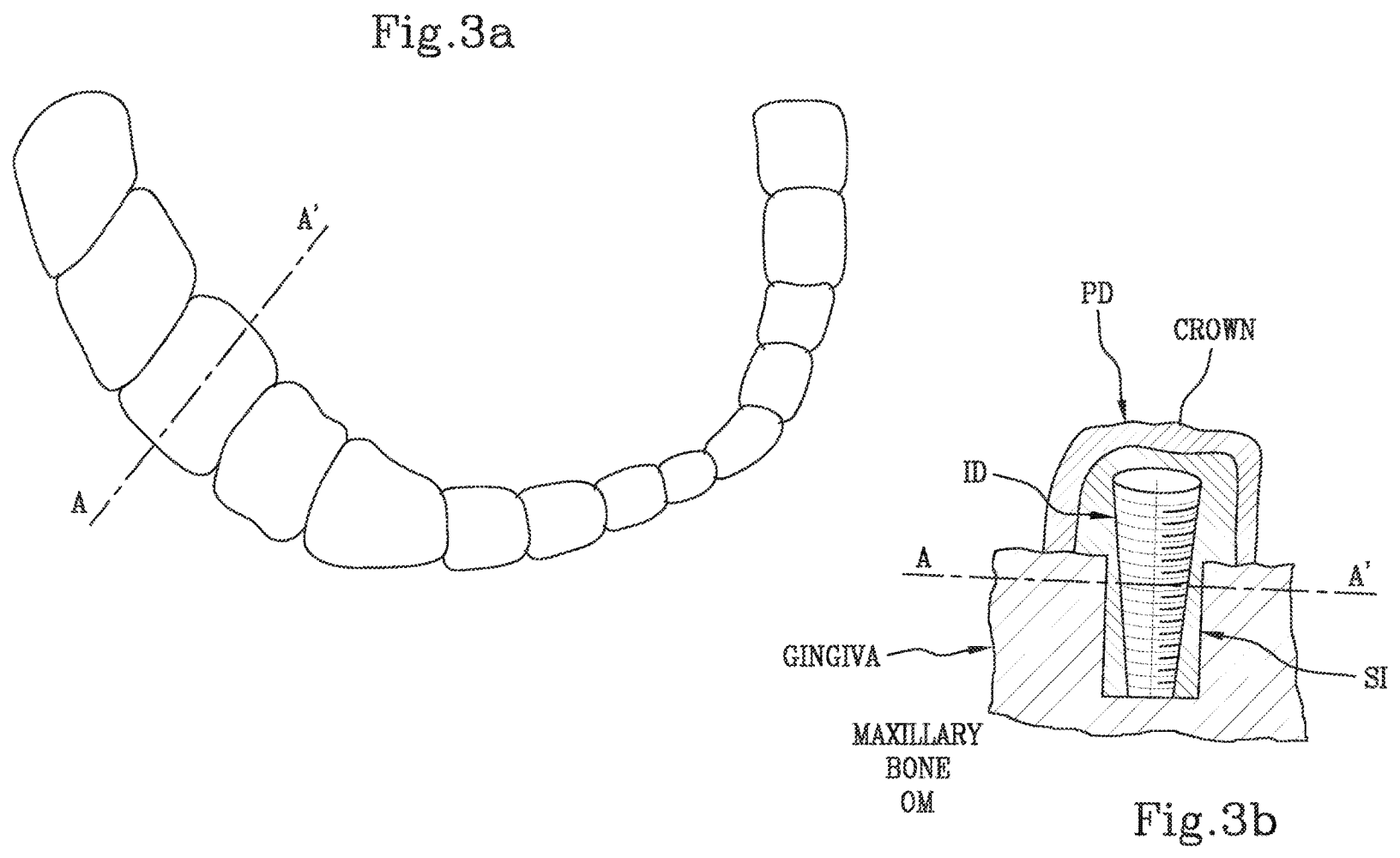
Figure 3C:
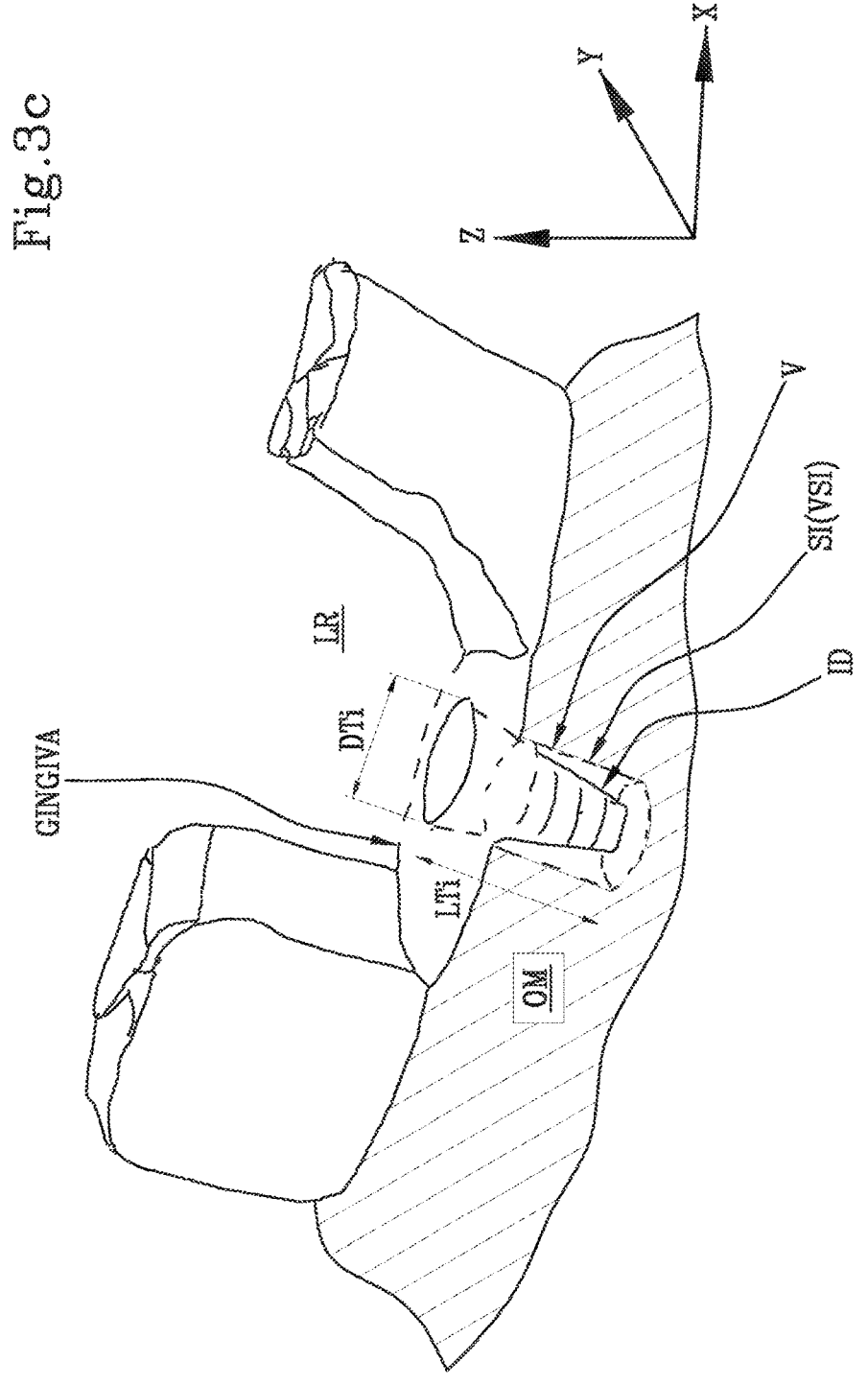
FIG. 3C schematically shows a dental implant in a maxillary arch according to the present invention.
Figure 7:
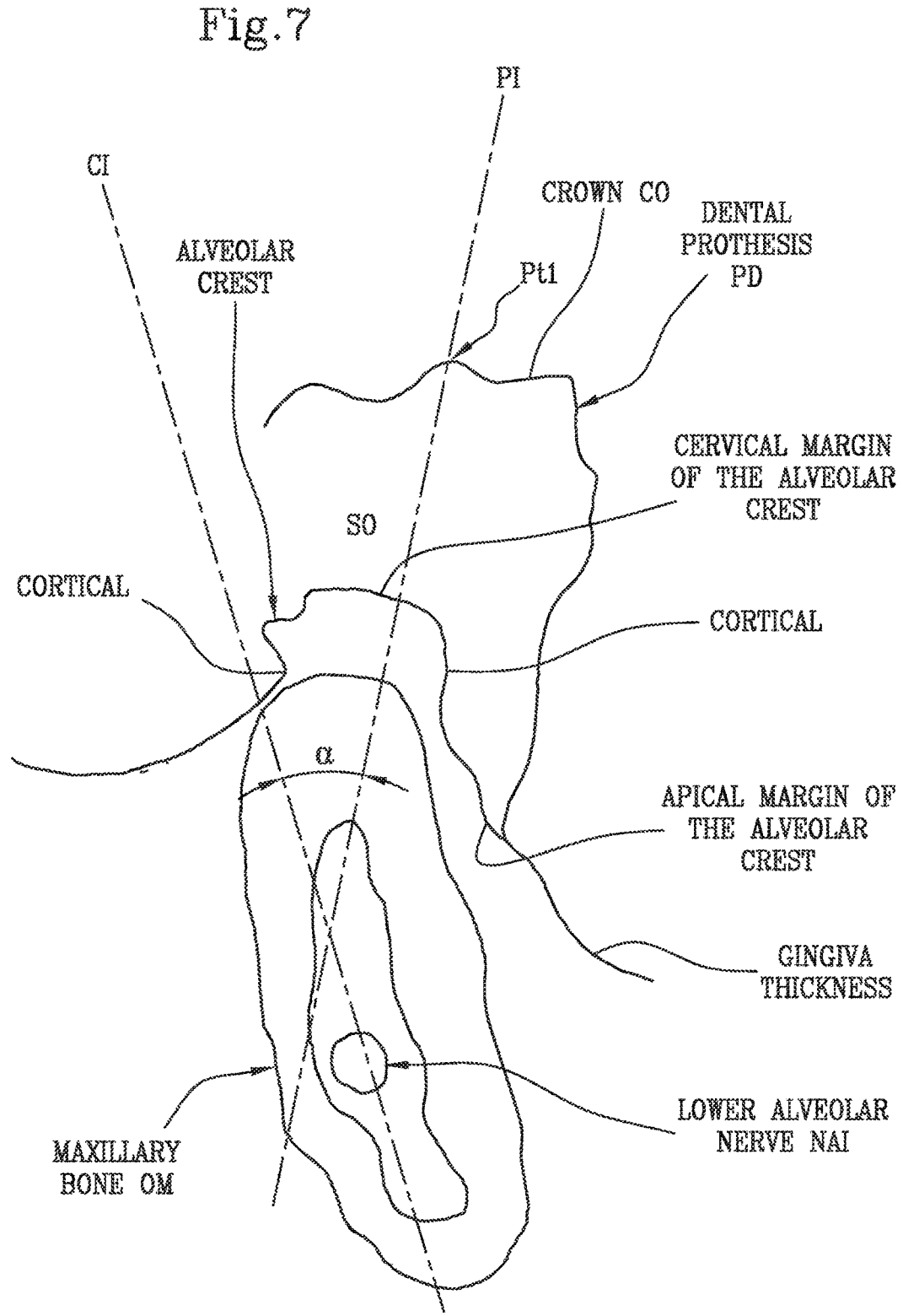
FIG. 7 shows a schematic view of a mandibular bone and of a simulated dental prosthesis.

With particular reference to FIGS. 1, 3A and 3C, the method comprises a step f1 of graphically simulating an anatomy of an envisaged dental prosthesis PD coupleable to a dental implant ID which can be inserted into a maxillary bone OM.

In particular, the simulation also shows an edentulous site LR (FIG. 3C) wherein the dental prosthesis PD corresponding to an identified tooth Tn is provided.

The invention applies both in case the tooth Tn is missing in the edentulous site, as well as if the tooth Tn is present in the edentulous site and must be rehabilitated.

As shown in FIG. 3A, the dental implant ID is installed in a maxillary bone OM at the base of the edentulous site LR (FIG. 3C), in a position occupied by the identified tooth Tn, in which Tn is the tooth identified in integrity conditions of the patient's mouth.

Preferably, the graphical simulation step f1 is performed by means of a CT scan of the oral cavity which provides data to perform a 3D reconstruction of the maxillary bones.

Alternatively or in addition, the graphic simulation is performed by means of a traditional dental prosthesis model or which may also be obtained by intra or extra-oral scanning or be virtually modeled.

An integrated graphic simulation is obtained by combining the intra or extra-oral or virtually-derived scanning with the 3D reconstruction obtained via CT scans.

Worded differently, and in sum, the graphic simulation step f1 is performed via computer-implemented graphic simulation means, particularly by way of a computer-implemented graphic simulation apparatus.

All the processing carried out are feasible starting from the first simulation step f1, without which it would not be possible any precise detection of the state of the oral cavity; non-automated detections, based essentially on the clinician's clinical expertise, are fully unappropriate for the subsequent steps of the simulation and can in no way lead to obtaining an optimized implant site.

In other words, the first simulation step f1 defines a computer-implemented mathematical graphic model wherefrom it is possible to perform innovative elaborations of the invention in order to obtain a precise and optimized simulation in terms of implementation of an implant site; the implant site thus obtained will be configured for being coupled with a corresponding dental implant.

To perform the simulation, the system of the invention comprises a first simulation station 1 designed to graphically simulate an anatomy of an envisaged dental prosthesis PD and a respective edentulous site LR corresponding to an identified tooth Tn, wherein the intended dental prosthesis PD is coupleable to a dental implant ID insertable into the maxillary bone OM.

With reference to FIG. 1, the invention further provides a step f2 of simulating an optimized implant site SI for the dental implant ID as a function of implant parameters PIMP of the dental implant ID and of first representative parameters PSI of the optimized implant site.

The simulation performed by the invention achieves technical functions typical of modern engineering work. It provides for realistic prediction of the performance of a dental implant in respect to the designed implant site which shall accommodate the former, and thereby ideally allows the dental implant to be developed so accurately such that a prototype's chances of success can be assessed before it is built.

The technical result increases with the speed of the simulation method, as this enables a wide range of designs to be virtually tested and examined for suitability before the expensive implant fabrication process starts.

The technical result increases with the speed of the simulation method, as this enables a wide range of designs to be virtually tested and examined for suitability before the expensive implant fabrication process starts.

Without a suitable technical support, an advanced test on a complex dental implant and/or a careful selection among many different designs would not be possible, or at least not feasible within a reasonable time.

It follows that computer-implemented simulation methods for virtual testing represent a practical and practice-oriented part of the dentist's or healthcare professional's or treatment provider's toolkit. What makes them so important is the fact that there isn't a purely mathematical, theoretical or mental method which is capable of providing a complete and/or fast prediction of a dental implant performance according to the parameters of the invention, that is different or diversifiable for each single patient.

In particular, the invention provides a simulation of an optimized implant site SI performing a simulation of a patient's damaged oral cavity and defines an implant site suitable for receiving a dental implant necessary to repair the highlighted damage.

In order to perform the simulation, the system of the invention comprises a second simulation station 10 designed to simulate, according to a computer-implemented graphic mode, the optimized implant site SI for the dental implant ID as a function of implant parameters PIMP of the dental implant ID and of the first parameters PSI of the optimized implant site.

In FIG. 4A some simulated parameters of the optimized implant site are shown in tabular form.

With reference to FIG. 3C, the optimized implant site SI has an at least partially cylindrical volumetric shape VSI inscribed within an envisaged circumscribing volume V.

In more detail, for the purpose of simulating the implant site SI, with reference to FIGS. 7 to 10, the method of the invention provides for calculating an ideal prosthetic axis PI for the envisaged dental prosthesis PD as a function of the graphic simulation performed by the first simulation station 1.

As described in the Italian priority applications in the name of the same Applicant, by ideal prosthetic axis it is meant an axis crossing an ideal point of the envisaged dental prosthesis PD as a function of the type of tooth considered.

In particular, in a first case of molar and premolar teeth (FIG. 5), the ideal prosthetic axis PI for the envisaged dental prosthesis PD is obtained as the axis passing through the center pt1 of the envisaged dental prosthesis PD.

In particular, in a second case of incisor, lateral and canines teeth (FIG. 12), the ideal prosthetic axis PI for the envisaged dental prosthesis PD is obtained as the axis passing through the palatal vertex pt2 of a triangle that schematizes the occlusal surface of the envisaged dental prosthesis PD.

In other words, in a first case of molar and premolar teeth, the ideal point pt1 will be at the center of the dental prosthesis PD and the crown CO, whereas, in a second case of anterior (incisor, lateral and canine) teeth, the ideal point pt2 will be at the apex of the palatal angle.

In both cases, for the calculation of this axis, the method involves obtaining two pairs of measurements of the simulated dental prosthesis PD, in particular a first pair of cervical measures and a second pair of apical measurements that are defined in terms of statistical data dependent on the position of the tooth and the anatomy of the arch opposed to that in which the dental prosthesis PD is being inserted.

The pair of measurements is calculated in the vestibulo-language and antero-posterior direction.

More in detail, the first pair of measurements is performed at the crown of the dental prosthesis PD and in the vestibular-tongue and anterior-posterior direction.

The second pair of measurements is performed at the collar of the dental prosthesis PD and in the vestibular-tongue and anterior-posterior direction.

Alternatively or additionally, the pair of measurements is calculated in a mesiodistal direction.

In more detail, the first pair of measurements is performed at the crown of the dental prosthesis PD, whereas the second pair of measurements is performed at the collar of the dental prosthesis PD.

The method involves calculating the prosthetic axis PI as a straight line passing through the intersection points of the segments of each pair of measurements.

Preferably, the ideal prosthetic axis also passes through a second point at the cervical level that corresponds to the center of the tooth for premolars and molars and at the apex of the triangle for the anterior teeth.

Based on same priority applications, by ideal axis it is meant an axis configured to perform an ideal halving of the bone quantity of the maxillary bone OM at an edentulous site LR.

Figure 8:
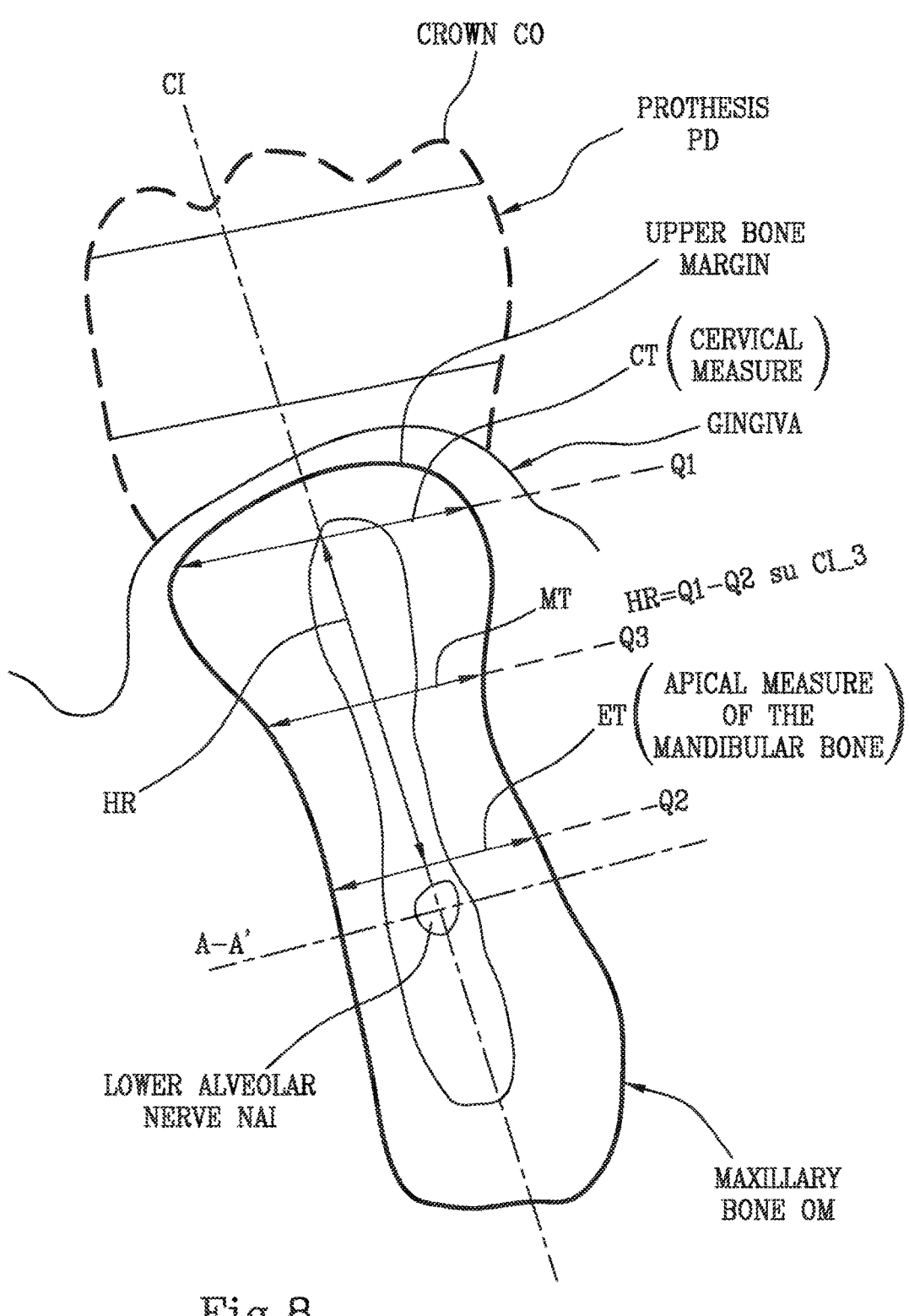
FIG. 8 is a schematic view of greater detail of FIG. 7.

With particular reference to FIG. 8, the method further provides for calculating a first cervical distance CT and a first apical distance ET of the maxillary bone OM at the edentulous site LR as a function of the graphic simulation in which the distances are calculated in a first direction relative to the maxillary bone OM.

Figures 9, 9A:
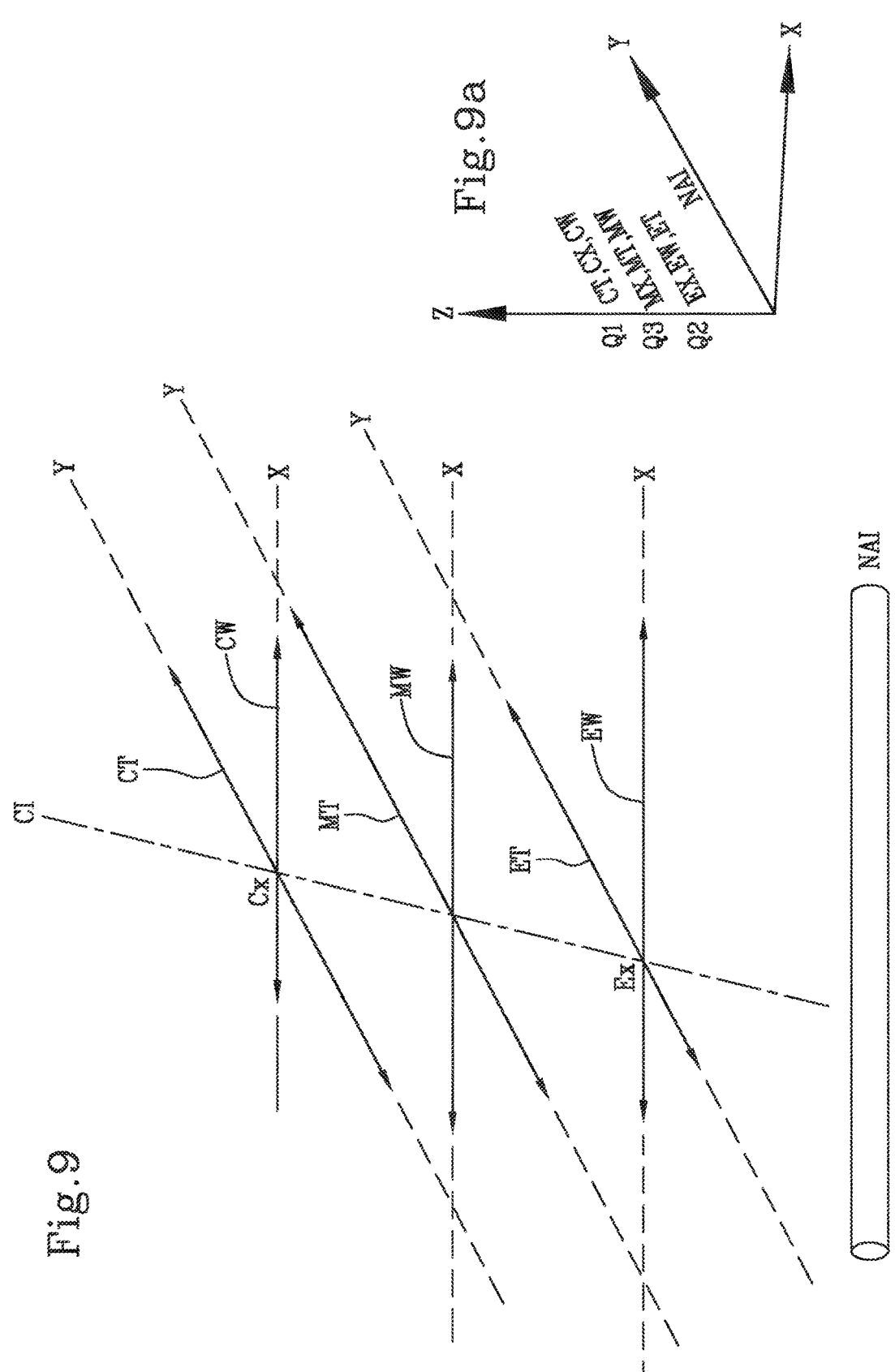
FIG. 9 is a schematic view of representative measurements of the mandibular bone with respect to an ideal surgical axis.
FIG. 9A shows a reference system for the measurements of FIG. 9.
Figure 10:
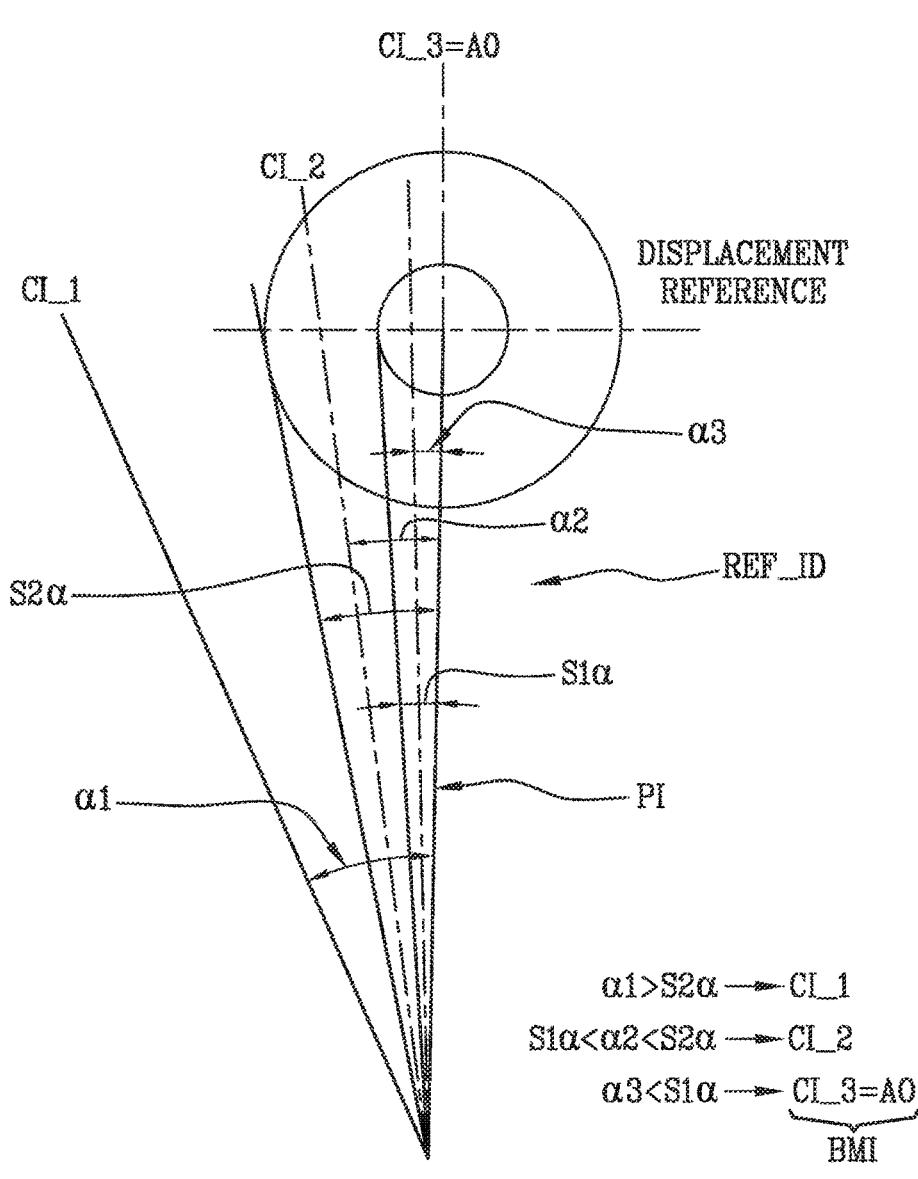
FIG. 10 is a schematic representation of reciprocal positions of ideal surgical axes and a prosthetic axis.

With particular reference to FIG. 9, the method further provides for calculating a second cervical distance CW and a second apical distance EW of the maxillary bone OM at the edentulous site LR as a function of the graphical simulation, in which the distances are calculated in a second direction to the maxillary bone OM.

Preferably, the first cervical distance CT is detected at a first cervical height q1 with respect to a reference height, e.g. relative to the upper bone margin, visible in FIG. 6.

Preferably, the first apical distance ET is detected at a first apical height q2 with respect to a reference height, in particular with respect to the inferior maxillary nerve NAI in the posterior mandible, or to another anatomic structure to be taken into account.

The method further provides to calculate an ideal surgical axis CI (FIG. 8) on the maxillary bone OM as a function of the cervical distances CT, CW and the apical distances CW, EW.

The steps described so far for the simulation of the implant site SI are performed taking into account that the ideal prosthetic axis PI and the ideal surgical axis CI determine a reference system REF_ID (FIG. 10) for the dental implant ID and that the ideal axis prosthetic PI and the ideal surgical axis CI are offset by an offset angle α.

The method further provides for calculating a bone height HR of the maxillary bone OM as a function of the calculated first cervical distance CT and first apical distance ET, wherein the bone height HR is representative of a bone availability of the maxillary bone OM at the edentulous site LR.

The method further provides to move the ideal surgical axis CI by determining a compromise surgical axis CI_i (i=1 . . . n) (FIG. 10) corresponding to a variable deviation angle αi (i=1 . . . n) relative to the ideal prosthetic axis PI.

According to the invention, the simulation is performed at least according to the implant parameters PIMP.

The implant parameters PIMP comprise at least:

the identified tooth Tn;

the first cervical distance CTi and the first apical distance ETi;

the second cervical distance CWi and the second apical distance EWi;

the first bone height HRi;

the variable deviation angle αi.

In particular, the first cervical distance CTi and the first apical distance ETi of the maxillary bone OM are simulated at the edentulous site LR, corresponding to the envisaged dental prosthesis PD, in a first direction with respect to the maxillary bone OM.

In particular, the second cervical distance CW and the second apical distance EW of the maxillary bone OM are simulated at the edentulous site LR, corresponding to the envisaged dental prosthesis PD, in a second direction with respect to the maxillary bone OM.

In particular, the first bone height HRi is representative of a bone availability of the maxillary bone OM at the edentulous site LR.

In particular, the variable deviation angle αi is included between the ideal surgical axis CI of the maxillary bone OM and the ideal prosthetic axis PI passing through the dental prosthesis PD.

According to the invention, the simulation is also carried out as a function of the first representative parameters PSI of the optimized implant site SI.

The first representative parameters PSI of the optimized implant site SI include at least:

a diameter DTi of the at least partially cylindrical volumetric shape VSI;

a height LIi of the at least partially cylindrical volumetric shape VSI;

According to the invention, the first representative parameters PSI exhibits variable values as a function of the variable deviation angle αi and of a global rating R.

The first representative parameters PSI include one or more rating values (Rαi, RDT, RLI, RRLRC, RPO, RDO) of the optimized implant site SI defined as a function of a comparison between the first representative parameters PSI and reference threshold values.

The optimized implant site SI is identified with a global rating R defined as a combined function of one or more of the rating values (Rαi, RDT, RLI, RRLRC, RPO, RDO).

In particular, the simulation of the optimized implant site SI is implemented according to the global rating R of the optimized implant site SI defined as a function of one or more of:

a deviation angle rating R_αi of said deviation angle αi;

a rating of diameter R_DT of the diameter DT;

a length rating R_LI of the length measurement LI of the optimized implant site SI;

a crown/root ratio rating R_RL_RC;

a rating of implant percentage in the bone R_PO;

a bone density rating R_DO.

where the rating values Rαi, RDT, RLI, RRLRC, RPO, RDO of the optimized implant site SI are defined based on a comparison between the current values αi, DT, LI, RLRC, PO, DO and respective reference thresholds.

Worded differently, the global rating R of the optimized implant site SI is indicative of the compliance of the optimized implant site SI with predefined reference thresholds of the first representative parameters PSI.

The invention provides a step f3 of calculating a plurality of dental implants MIi as a function of comparing at least the first parameters PSI of the optimized implant site SI and representative parameters PIE of existing dental implants.

Preferably, as shown in FIG. 1, the parameters PIE are stored in a database IE.

In particular, with reference to FIG. 1, to calculate the plurality of dental implants MIi, the calculation is performed by a first processing station 40 configured to calculate a plurality of dental implants MIi as a function of comparing at least the first parameters PSI of the optimized implant site SI with representative parameters PIE of existing dental implants.

The invention provides a subsequent step f4 of calculating a plurality of optimal dental implants BMIii as a function of comparing between the first representative parameters PSI and the second representative parameters PIE when the global rating R of the optimized implant site SI is minimized.

In other words, the invention provides identifying a dental implant ID for the optimized implant site SI which performs a simulation of a patient's damaged oral cavity, and defining a plurality of optimal dental implants BMIi applicable to such optimized implant site SI.

In particular, with reference to FIG. 1, the system of the invention comprises a first processing station (40) capable of calculating parameters of a plurality of optimal dental implants BMIi as a function of comparing between at least the parameters of the optimized implant site PSI and the representative parameters PIE of existing dental implants based on a minimized rating R of the optimized implant site PSI, wherein the rating R is indicative of the optimized implant site PSI being in compliance with predefined reference thresholds of the representative parameters PSI.

FIG. 4B shows some calculated optimal dental implants BMIi in table form, in particular a first optimal implant BMI0, a second optimal implant BMI1 and a third optimal implant BMI2, based on respective calculated parameters.

The optimal dental implants BMIi are characterized by PBMI parameters.

Preferably, with reference to FIG. 5, the parameters PBMI comprise:
    an identified tooth Tn;
    a diameter DTi of the at least partially cylindrical volumetric shape VSI;
    a height L1 of the at least partially cylindrical volumetric shape VSI;
    a deviation angle $\alpha$;
    an overall rating R.
    Preferably,
    an Ub identifier of the system manufacturer (brend)
    an Um identifier of the implant model.

With particular reference to FIG. 1, after having identified the optimal usable implants, the invention advantageously provides a step f5 of selecting a usable implant UI from the plurality of optimal dental implants BMIi.

In other words, the usable implant UI is defined as a function of the optimal dental implants BMIi, i.e. UI=f (BMij).

In order to obtain the selection, with reference to FIG. 1, the system of the invention comprises a second processing station 30 comprising in turn a first calculation unit 301 adapted to select the usable implant UI from the plurality of optimal dental implants BMIi.

Preferably, selection is made based on a clinician's clinic expertise.

The usable implant UI will be characterized by first parameters PUI.

Preferably, with reference to FIG. 5, the first parameters PUI comprise:
    an identified tooth UTn;
    a diameter UDTi of the at least partially cylindrical volumetric shape VSI;
    a height ULIi of the at least partially cylindrical volumetric shape VSI;
    a deviation angle $U\alpha$;
    a global rating value UR.
    Preferably, the first parameters PUI further comprise
    an Ub identifier of the implant manufacturer (brend)
    an Um identifier of the implant model.

FIG. 5 depicts the first parameters PUI in tabular form as well as the simulated parameters of the optimized implant site.

The invention further provides a step f6 of calculating first deviations $\Delta$UIi between the parameters of the optimized implant site PSI and the first parameters PUI of the usable implant UI.

The technical effect achieved is an estimate of the conformity between the parameters automatically calculated for the optimized implant site SI and the parameters of the usable implant obtained also as a function of the clinician's clinic expertise; this allows having a first matching between the simulated implant and the implant actually used.

To perform the calculation, the second processing station 30 comprises a second calculation unit 302 (FIG. 1) capable of calculating first deviations $\Delta$UI between the parameters of the optimized implant site PSI and the first parameters PUI of the usable implant UI.

FIG. 6 shows an example of first deviations $\Delta$UI in table form between the parameters of the usable implant UI and the simulated parameters of the optimized implant site SI.

The invention provides a further step f7 of calculating second deviations $\Delta$BMij between
    second parameters PBMij of the plurality of optimal dental implants BMIi not selected as usable implants UI, and
    the parameters of the optimized implant site PSI.

In particular, the calculation of the second parameters is performed on at least one first plurality P1 of optimal dental implants BMij.

According to the invention, the first plurality P1 of optimal dental implants BMij comprises a first plurality n of implants with rating RBMij next to the rating RPSI of the optimized implant site PSI.

This solution is provided in the case of a reduced number of optimal dental implants BMi, preferably with n being such that $3 < n < 5$.

In other words, the implants with the best rating are the ones taken into account, i.e. the ones being most proximate to the ideal case of the optimized implant site, regardless of respective rating values.

This solution may be defined as a proximity solution.

Alternatively, or in addition, the calculation of the second parameters is performed on at least one second plurality P2 of optimal dental implants BMij.

According to the invention, the second plurality P2 of optimal dental implants BMij comprises a second plurality m of optimal dental implants with rating RBMij being lower than a predefined R_pred rating value.

In other words, in the case of a high number of optimal dental implants BMi (e.g. 20) and with several optimal dental implants being proximate to the ideal case, the implants being most proximate to the ideal case are the ones selected according to a predefined rating value, for example R_pred<=1.5)).

In this case, there exists a number of BMI with almost coincident values.

This solution can be defined as a statistical solution.

The calculation of the second parameters is performed by the second processing station 30, in particular by a third processing unit 303 suitable for calculating second deviations ΔBMij between:

the second parameters PBMij of at least one plurality P1, P2 of optimal dental implants BMij of the plurality of optimal dental implants BMIi not selected as usable UI implants and the parameters PSI of the optimized implant site SI.

FIG. 6 shows examples of second deviations ΔBMij in table form between the parameters of optimal dental implants BMI and the simulated parameters of the optimized implant site SI.

The invention provides, at this point, a step f8 of calculating optimized real parameters PSIR of the optimized implant site SI in a combined function of the first deviations ΔUI and second deviations ΔBMij.

With reference to FIG. 1, a processing unit 304 is adapted to calculate the optimized real parameters PSIR of the optimized implant site SI.

The technical effect achieved is concerned with the determination of real and consolidated values based on which the sector guidelines are to be adapted.

Preferably, the method comprises a further step f9 of overlapping the optimized implant site SI, defined in step f8 as a function of the calculated real optimized parameters PSIR, on the optimized implant site SI simulated in step f2 as a function of the implant parameters PIMP and the first parameters PSI of the optimized implant site SI.

The technical effect achieved is a verification of the stability of the biological result obtained (bone volumes) in the application of the method/monitoring system of the invention.

This makes it possible to overlap a real post-production reconstruction of the dental implant to the original simulation.

The second processing station 30 comprises, for this purpose, an overlapping module 305 (FIG. 1) configured to overlap the optimized implant site SI, defined in step f8, on the optimized implant site SI simulated in step f2, in order to obtain the effects described herein.

In particular, the overlapping module 305 is configured to execute step f9 of overlapping:

said optimized real parameters PSIR of the optimized implant site SI calculated from said fourth calculation unit 304 as a combined function of said first deviations ΔUI and said second deviations ΔBMij, with said optimized implant site SI, simulated according to a computer-implemented graphic mode, for said dental implant ID as a function of said implant parameters PIMP of said dental implant ID and of first parameters PSI of said optimized implant site SI, thus causing an overlapping between original simulation and actual post-production reconstruction of the dental implant.

According to the invention, the step of calculating the optimized real parameters PSIR of the optimized implant site SI provides various implementation solutions.

In a first solution, calculating actual optimized parameters PSIR comprises a step f71 of comparing the first deviations ΔUI and the average M of the second deviations ΔBMij.

Figures 2A, 2B, 2C:
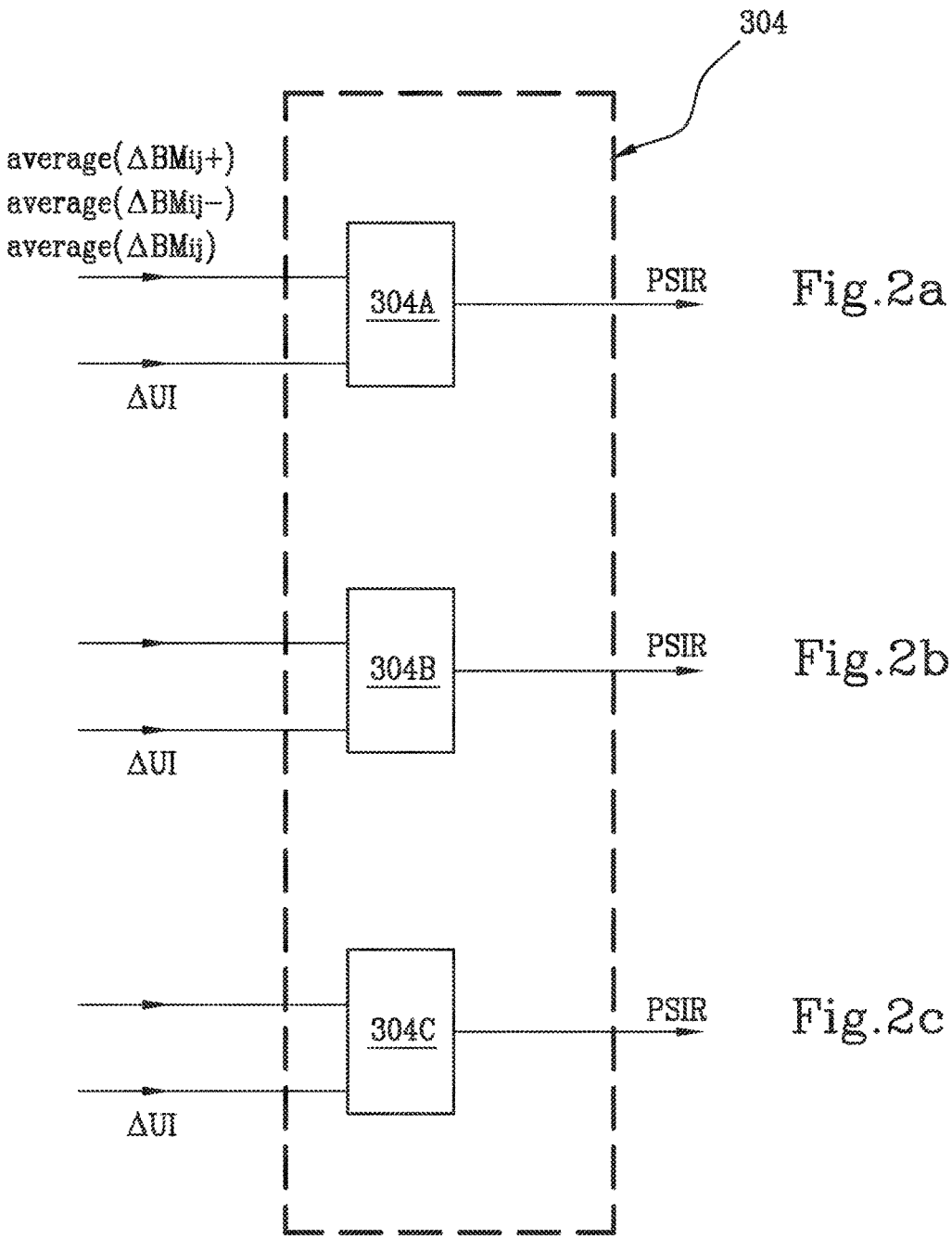
FIGS. 2a-2c provide a detail of a portion of the block diagram of FIG. 1.

As shown in FIG. 2, a first calculation module 304A in the processing unit 304 is configured to perform the step f71.

Preferably, the step f71 of comparing the first deviations ΔUI and the average M of the second deviations ΔBMij, includes the sub-steps of:

calculating the average M of the second deviations ΔBMij comparing the value of the average M calculated together with the values of the first deviations ΔUI;

calculating the optimized real parameters PSIR as a function of the comparison.

In more detail, in the comparison step f71, if the value of the calculated average M is lower than the first deviations ΔUI, i.e. if the module of the average M is smaller than the first deviations ΔUI, the step f71 provides a further sub-step of calculating the optimized real parameters PSIR by modifying the parameters of the optimized implant site PSI with the value of the average M of the second deviations ΔBMij being summed or substracted.

In other words, PSIR=PSI+|M|.

In this calculation of the optimized real parameters PSIR, all values of the second deviations ΔBMij are taken into account when calculating the average M with the respective marks, i.e. the values of the second deviations taken into account can be positive or negative relative to the parameters of the optimized implant site.

According to variants of the first solution, the step f7 of calculating second deviations ΔBMij comprises:

calculating second positive deviations ΔBMij+ and/or second negative deviations ΔBMij− defined respectively as a function of a diameter value of the optimal implant BMIi being greater or smaller than the value of the diameter of the optimized implant site PSI;

calculating optimized real oversized parameters PSIR+ and/or optimized real undersized parameters PSIR—of the optimized implant site SI as a combined function of the first deviations ΔUI and second positive ΔBMij+ or negative ΔBMij− deviations respectively.

In particular, in a first variant of the first solution, the third processing unit 303 is able to calculate second positive deviations ΔBMij+ between:

the second parameters PBMij of at least one plurality P1, P2 of optimal dental implants BMij of the plurality of optimal dental implants BMIi not selected as usable implants UI the parameters PSI of the optimized implant site PSI.

The calculation is made when the diameter value of the optimal implant is greater than the value of the diameter of the optimized implant site PSI.

At this stage, the invention provides, based on aforementioned step f8, calculating optimized real oversized parameters PSIR+ of the optimized implant site SI as a combined function of the first deviations ΔUI and second positive deviations ΔBMij+.

With reference to FIG. 1, the processing unit 304 is able to calculate the optimized real oversized parameters PSIR+ of the optimized implant site SI.

In this variant the calculation of optimized real oversized parameters PSIR+ takes into account only the positive values of the second ΔBMij deviations for calculating the average M with respect to the parameters values of the optimized implant site.

In particular, in a second variant of the first solution, the third processing unit 303 is suitable for calculating second negative deviations ΔBMij− between:

the second PBMij parameters of at least one plurality P1, P2 of optimal dental implants BMij of the plurality of optimal dental implants BMIi not selected as usable implants UI the parameters PSI of the optimized implant site PSI.

The calculation is made when the value of the optimal implant diameter is less than the value of the optimized implant site diameter PSI.

At this stage, the invention provides, based on aforementioned step f8, calculating optimized real oversized parameters PSIR—of the optimized implant site SI as a combined function of the first deviations ΔUI and second negative deviations ΔBMij-.

With reference to FIG. 1, the processing unit 304 is adapted to calculate the optimized real oversized parameters PSIR—of the optimized implant site SI.

In this variant the calculation of the optimized real undersized parameters PSIR-takes into account only the negative values of the second deviations ΔBMij for calculating the average M with respect to the parameters value of the optimized implant site.

In a second solution, calculating optimized real parameters PSIR comprises a step f72 of comparing the first deviations ΔUI and the median MD of the second deviations ΔBMij.

As shown in FIG. 2, a second calculation module 304B in the processing unit 304 is configured to perform step f72.

As is known, the median is the value that occupies the central position in an ordered set of data.

The median is a measure which is little affected by the presence of abnormal data and due to this it is used when one wishes to mitigate the effect of extreme values.

The step f72 of comparing the first deviations ΔUI and the median (MD) of the second deviations ΔBMij comprises the steps of:

calculating if the median MD of the second deviations ΔBMij is smaller than the first deviations ΔUI;

comparing the value of the median MD calculated together with the values of the first deviations ΔUI;

calculating the optimized real parameters PSIR as a function of the comparison.

In more detail, following the comparison step, where the value of the calculated median MD is smaller than the first deviations ΔUI, i.e. if the median module MD is smaller than the second deviations ΔBMij, the step f72 provides an additional sub-step of calculating the optimized real parameters PSIR by modifying the parameters of the optimized implant site PSI with the value of the median MD being added or subtracted.

In other words, PSIR=PSI+|MD|

In a third solution, calculating real optimized parameters (PSIR) comprises a step f73 of comparing the first deviations ΔUI and the mode MO of the second deviations ΔBMij.

As shown in FIG. 2, a third calculation module 304C, within the processing unit 304, is configured to execute step f73.

As is known, the mode is the most recurring value in a data set.

The step f73 of comparing the first deviations ΔUI and the mode MO of the second deviations ΔBMij, comprises the steps of:

calculating if the mode MO of the second deviations ΔBMij is smaller than the first deviations ΔUI;

comparing the value of the mode MO calculated with the values of the first deviations ΔUI;

calculating the optimized real parameters PSIR according to the comparison.

More in detail, following the comparison sub-step, if the calculated value of the mode MO is lower than the first deviations ΔUI, i.e. if the modulus of the median MO is smaller than the second deviations ΔBMij, the step f72 provides a further sub-step of calculating the optimized real parameters PSIR by modifying the parameters of the optimized implant site PSI by summing or subtracting the mode MO value.

The PSIR values obtained in one or more of the described modalities guarantee the technical effect of an objective identification in respect to an actual optimal dental implant thereby making it possible to adapt the guidelines on which dental implant construction is based, to optimal real and objective values.

According to the invention, the described monitoring method is adapted to be computer-implemented.

The invention further provides a computer program which, when in use on a processing means, performs one or more of the steps of the computer-implemented method.

According to the invention, the optimal real dental implant ID, described above, is adapted to be realized as a function of the optimized real parameters PSIR according to one of the solutions shown.

In general it should be noted that in the present context and in the subsequent claims, the first processing station 40, the second processing station 30 and the processing unit 304 are described as divided into separate functional modules (memory modules or operating modules) at the only purpose of describing the functions in a clear and complete manner.

Indeed, such processing stations/units may consist of a single electronic device, suitably programmed to perform the described functions, and the different modules may correspond to hardware entities and/or software routines being part of the programmed device.

Alternatively or additionally, such functionalities may be performed by a plurality of electronic devices whereon said functional modules can be distributed.

The processing stations/units may also use one or more processors to execute the instructions contained in the memory modules.

The aforementioned functional modules may also be distributed on different computers locally or remotely depending on the architecture of the network they reside in.

The systems further comprise all memory and/or operating modules and/or means required to implement the functions as described in the methods thereof.

The invention claimed is:

1. A computer-implemented method of identifying at least one dental implant for an implant site, the method comprising:

graphically simulating, via a computer-implemented graphic simulation, a simulated dental prosthesis and a respective edentulous site corresponding to an identified tooth, wherein said simulated dental prosthesis is simulated to be couplable to a dental implant that is insertable into a maxillary bone at the edentulous site;

simulating a simulated implant site in said maxillary bone, wherein said simulated implant site has an at least partially cylindrical volumetric shape inscribed in a circumscribing volume, said simulating being performed as a function of at least said identified tooth, a cervical distance of said maxillary bone at said edentulous site, an apical distance of said maxillary bone at said edentulous site, a bone height of said maxillary bone at said edentulous site, and a variable deviation angle;

wherein the simulated implant site is further simulated as a function of first representative parameters thereof comprising at least a diameter of said at least partially cylindrical volumetric shape and a height of said at least partially cylindrical volumetric shape, wherein said first representative parameters have respective values varying as a function of said variable deviation angle;

providing a database comprising sets of second representative parameters that define respective existing dental implants;

comparing said first representative parameters with said second representative parameters; and identifying one or more optimal dental implants for said simulated implant site as a result of the comparison between said first representative parameters and said second representative parameters.

2. The method of claim 1, further comprising:

calculating an ideal prosthetic axis for said simulated dental prosthesis as a function of said graphic simulation, wherein said ideal prosthetic axis is an axis crossing an ideal point of the simulated dental prosthesis as a function of the identified tooth;

calculating the cervical distance and the apical distance of said maxillary bone at said edentulous site as a function of said graphic simulation, wherein the cervical distance and the apical distance are calculated in a first direction relative to said maxillary bone, and wherein said cervical distance is detected at a cervical portion with respect to a reference portion;

calculating an ideal surgical axis on said maxillary bone as a function of said cervical distance and said apical distance, wherein said ideal surgical axis is an axis configured to perform an ideal halving of a bone quantity of the maxillary bone at the edentulous site, wherein the ideal prosthetic axis and the ideal surgical axis define a reference system for said dental implant, and wherein said ideal prosthetic axis and said ideal surgical axis are offset by a deviation angle;

calculating a bone height of said maxillary bone as a function of said cervical distance and said apical distance, wherein said bone height is representative of a bone availability of said maxillary bone at said edentulous site; and moving said ideal surgical axis so as to determine a surgical compromise axis corresponding to the variable deviation angle with respect to said ideal prosthetic axis.

3. The method according to claim 1, wherein said first representative parameters further comprise one or more rating values of said optimized implant site defined as a function of a comparison between said first representative parameters and reference threshold values, wherein said optimized implant site is identified with a rating defined as a combined function of said rating values.

4. The method according to claim 1, wherein the database comprises said second representative parameters representative of a tooth identifier for an existing implant, an implant diameter for an existing implant, an implant height for an existing implant, a deviation angle for an existing implant, a rating identifier for an existing implant, an implant manufacturer, and an implant model.

5. The method according to claim 4, wherein the one or more optimal dental implants are identified as a function of the comparison between said first representative parameters and said second representative parameters when said rating is minimized.

6. The method according to claim 5, wherein minimizing said rating comprises comparing said deviation angle with predefined threshold values of deviation angles comprising a first predefined deviation angle threshold value and a second predefined deviation angle threshold value, wherein the first predefined deviation angle threshold value is less than the second predefined deviation angle threshold value.

7. The method according to claim 6, wherein comparing said deviation angle comprises recalculating said bone thickness and moving said surgical axis with respect to said ideal prosthetic axis maintained in a fixed position, so as to bring about a reduction in said variable deviation angle, wherein said recalculating and said moving are performed as long as the variable deviation angle remains greater than said first default threshold value of the deviation angle, said deviation angle being minimized when it is less than said first default threshold value of the deviation angle.

8. The method according to claim 7, further comprising:

assigning a rating to said implant site as a function of said comparing said variable deviation angle with the default threshold value of the deviation angle, wherein said rating decreases as the deviation angle decreases and tends towards zero as the deviation angle tends towards its optimized value, wherein said assigning a rating includes moving the surgical axis, calculating a bone height of said bone, recalculating said first and second cervical distances and said first and second apical distances as a function of said variable deviation angle, identifying a corresponding optimal implant site, and identifying corresponding optimal dental implants.

9. The identification method according to claim 8, comprising at least one of:

assigning a rating to a measure of said diameter of said at least partially cylindrical volumetric shape or said implant diameter based on a comparison between said diameter and one or more default diameter threshold values;

or assigning a rating to said height measurement as a function of a default height threshold value;

or assigning a rating to said crown/root ratio based on a comparison between said crown/root ratio and one or more thresholds;

or assigning a rating to said implant percentage within the bone based on a comparison between said implant percentage within the bone and one or more thresholds;

or assigning a rating to said bone density based on whether or not the bone density is greater than a density threshold.

\* \* \* \* \*